United States Patent
Bhattacharjee et al.

(10) Patent No.: US 8,054,091 B2
(45) Date of Patent: Nov. 8, 2011

(54) ANALYSIS OF THIN LIQUID FILMS

(75) Inventors: Subir Bhattacharjee, Edmonton (CA);
Farshid Karimi Mostowfi, Edmonton (CA); Jacob Masliyah, Edmonton (CA);
Jan Czarnecki, Edmonton (CA);
Elizeusz Lucjusz Musial, Krakow (PL)

(73) Assignee: The Governors of the University of Alberta, Edmonton (CA)

( * ) Notice: Subject to any disclaimer, the term of this patent is extended or adjusted under 35 U.S.C. 154(b) by 513 days.

(21) Appl. No.: 12/280,154

(22) PCT Filed: Feb. 21, 2007

(86) PCT No.: PCT/CA2007/000268
§ 371 (c)(1),
(2), (4) Date: Feb. 12, 2009

(87) PCT Pub. No.: WO2007/095739
PCT Pub. Date: Aug. 30, 2007

(65) Prior Publication Data
US 2009/0243635 A1    Oct. 1, 2009

Related U.S. Application Data

(60) Provisional application No. 60/775,151, filed on Feb. 21, 2006.

(51) Int. Cl.
*G01R 27/08* (2006.01)
(52) U.S. Cl. .. 324/698; 324/71.1; 210/746; 210/748.01; 210/695; 435/6
(58) Field of Classification Search ............ 324/698
See application file for complete search history.

(56) References Cited

U.S. PATENT DOCUMENTS

| | | | |
|---|---|---|---|
| 6,365,413 B1 | 4/2002 | Hall | |
| 6,756,791 B1 | 6/2004 | Bhushan | |
| 7,179,383 B1* | 2/2007 | Porter et al. | 210/695 |
| 2002/0023841 A1 | 2/2002 | Ahn | |
| 2002/0197603 A1* | 12/2002 | Chow et al. | 435/6 |
| 2005/0042615 A1* | 2/2005 | Smith et al. | 435/6 |

FOREIGN PATENT DOCUMENTS

JP    2001-264237 A    9/2001

OTHER PUBLICATIONS

Panchev, N. et al., "A New Method for Water-in-Oil Emulsion Film Studies", Colloids and Surfaces A: Physicochem. Eng. Aspects 315 (2008), Elsevier, pp. 74 -78, Jul. 25, 2007.*
International Search Report mailed Jun. 6, 2007, issued in corresponding International Application No. PCT/CA2007/000268, filed Feb. 21, 2007, 5 pages.

* cited by examiner

*Primary Examiner* — Timothy J Dole
*Assistant Examiner* — Benjamin M Baldridge
(74) *Attorney, Agent, or Firm* — Christensen O'Connor Johnson Kindness PLLC

(57) ABSTRACT

A novel microfluidic device has been developed to measure stability of thin liquid films of water in oil emulsions using electrochemical perturbation of interfaces. This new device can be utilized in rapid classification of de-emulsifiers used in petroleum industries. Although water/crude oil emulsions have been the primary focus of this research, this measurement platform can be used in other industries such as food, cosmetics and bio-engineering (bilayer lipid membranes) as well as environmental remediation of oil spills. The compact design of the device and replacement of the mechanical measurements such as pressure with electrical signal measurements contributes in substantial size reduction of the experimental platform so that it can be employed for onsite measurements in remote areas.

14 Claims, 10 Drawing Sheets

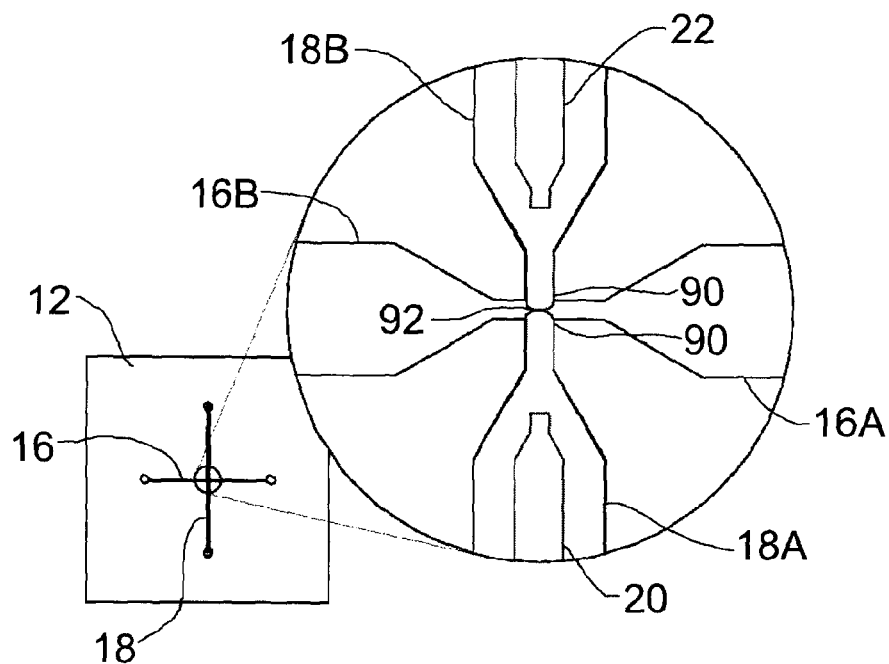
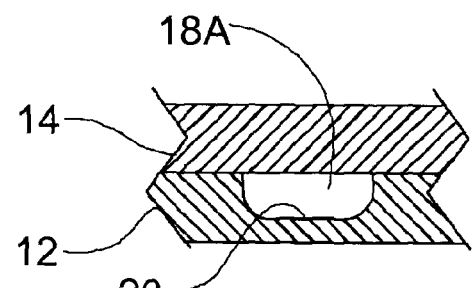
FIG. 1
FIG. 2
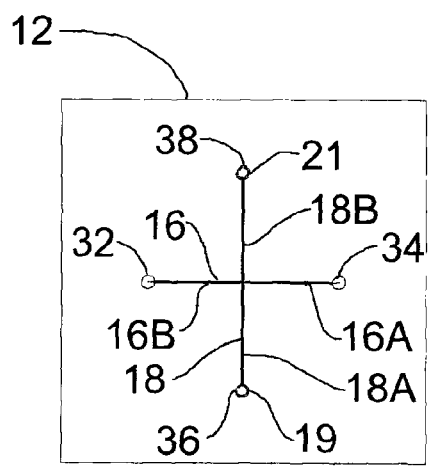
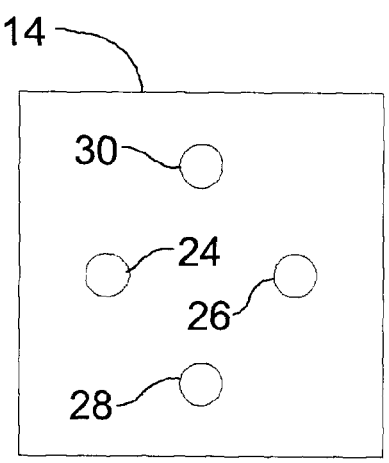
FIG. 3
FIG. 4

ANALYSIS OF THIN LIQUID FILMS

BACKGROUND

The common practice in industry, particularly the petroleum industry, to measure the effect of de-emulsifiers on the stability of emulsions is the so called "Bottle test". A glass bottle filled with measured amounts of oil (such as crude oil, bitumen, heavy oil, etc.), water and de-emulsifiers will be provided. After creating the emulsion by shaking the bottle, the emulsion will be left for a certain period of time so that the separation of the water from the oil can occur. The amount of water liberated from the emulsion is a measure of efficiency of the de-emulsifier. This test has to be repeated many times due to the different available de-emulsifiers and their wide spectrum of concentration. Furthermore, the type of crude oil varies from one reservoir to another, so finding the best match for every specific oil is a very time consuming task. "Bottle test" is inherently a low-tech which does not provide any insight about the film properties and its lack of automation reveals the need for a better measurement platform.

The presence of water droplets in crude oil can result in a very stable emulsion system. Stabilizer molecules in oil adsorb on the surface of the water droplets and make a resistant shield that prevents them from coalescence. Most of the water in such water-oil emulsions can be removed using density difference methods such as gravitational or centrifugal separations. However, the remaining 1 or 2% of the water that exists in the form of micro droplets (less than 5 μm) is difficult to separate using conventional techniques. The density difference methods do not separate such droplets due to insignificant gravitational or centrifugal forces. De-emulsifiers are used to increase the chance of coalescence of micron size droplets by means of reducing interfacial tension of the water/oil system. De-emulsifiers are generally complex polyelectrolytes or mixtures of polyelectrolytes, which specifically interact with the oil-water interfaces to destabilize emulsions. Therefore, the procedure of identifying the best de-emulsifiers for a specific type of oil using the "bottle test" may take days, which makes it quite difficult to change the amount or type of the de-emulsifier during production. Time is also very crucial in oil spill remediation issues, which underscores the need for better and faster de-emulsifier identification methods. Alternatively, the stability of these emulsion systems and the effect of de-emulsifiers can be studied experimentally on a thin film of oil formed between two water droplets. Experimental techniques such as the Thin Liquid Film (TLF) apparatus or the Sheludko cell, and the Micropipette experiment may be used to create thin liquid films and measure their characteristics. The thin liquid film of oil is ruptured using an external force such as pressure or electric field. The pressure or the electric field at which the film breaks is the measure of stability of the interface.

The thin liquid film apparatus (TLF) is a well-known and widely used method to create and study the stability of thin liquid films. It employs a porous glass plate in which a millimeter size circular hole is drilled. The plate is connected to a capillary, which is filled with oil. The plate is then immersed in an electrolyte solution. Simultaneous adjustment of the pressure of the electrolyte solution and the oil in the capillary results in formation of an oil film inside the hole. The film developed can be considered as an analogue of two large (millimeter scale) water droplets separated by a thin oil film. By increasing the electrolyte's pressure, the two water phases can be pushed toward each other, thereby altering the film thickness. Using interferometry techniques, the thickness of the film can be measured accurately. The micropipette method can also be used to study thin liquid films. It consists of two micropipettes, at the tips of which water droplets are formed. The two pipettes are immersed in the oil phase while pressing the two water droplets onto each other. The oil film created between the droplets can be broken by moving the micropipettes closer. This can result in characterization of the film stability. This method is not capable of measuring the thickness of the film directly.

SUMMARY

Microfluidics technology is a powerful tool to fabricate very small features such as channels and electrodes on glass or silicon substrates. The size of these channels can be as small as few microns which resembles the actual size of micron-sized droplets. The disclosed apparatus and method makes it possible, for the first time, to create thin liquid films between micron-sized droplets in a controlled manner, which corresponds to very high capillary pressures. Size reduction improves portability and reduces the cost. Due to reduction of the film's area, it also reduces unwanted perturbations on the film such as thermal fluctuations, leading to more accurate measurements. Due to integrated nature of micropatterning technology, parallel experimenting is possible with multi-channel chips, where one can form and break a few thin films at a time. Online measurement is another possibility provided by this technology. Since the chemistry and composition of the oil may change during processing in the production plant, a bypass line can be passed through the chip for real time measurement of stability of the emulsion. Consequently, these measurements can be used to modify the type and concentration of the de-emulsifier during oil production.

Practical applications of the disclosed apparatus and method include: a small microfluidic package connected to a laptop computer, which may be used as an onsite measurement tool to evaluate stability of thin films and/or efficiency of emulsifiers/de-emulsifiers for water in oil emulsions; an experimental platform for rapid classification of emulsifier/de-emulsifier in a measurement or research laboratory; and an online feed back control of a de-emulsifier feeder in an oil production facility.

There is provided a method of determining characteristics of a thin liquid film, the method comprising the steps of: establishing a thin film of a first liquid, such as oil, between fluids, such as aqueous fluids, in a microfluidic chip; and determining characteristics of the thin film from electrical properties of the thin film.

There is also provided a method of forming a thin liquid film of microscopic dimensions and measuring its interfacial properties, the method comprising the steps of: trapping the film forming liquid between two bulging droplets of a second liquid at the intersection of two microchannels; applying an electric field (potential difference) across the film to destabilize and break the film; and measuring the potential difference at which the film breaks, thereby allowing the assessment of the interfacial properties of the film and its stability.

In some applications, the film forming liquid is oil and the second liquid comprises an aqueous electrolyte solution. Additional molecules, such as surfactants, or nanoparticles may be added to either the film forming liquid or the second liquid. The additional molecules may be selected to adsorb at the interfaces of the two liquids and modify the interfacial behavior of the film. The pressure difference between the film forming liquid channel and the channel containing the second liquid may be controlled and may also be measured. In some embodiments, the liquid film may be compressed by application of a direct current (DC) electric potential difference across the film. Various techniques may be used to determine film rupture characteristics.

An apparatus for thin film analysis is also provided. In one embodiment, the apparatus provides channels in a microfluidic platform that intersect at a common point, and measuring elements are provided for measuring film characteristics at the common point. A drain may be provided at the common point, and the channels may taper towards the common point. Fluid control devices control fluid flow in the apparatus.

BRIEF DESCRIPTION OF THE FIGURES

Embodiments will now be described with reference to the figures, in which like reference characters denote like elements, by way of example, and in which:

FIG. 1 is a schematic layout of an exemplary embodiment of a microfluidic chip, with a detailed view of the intersection of the channels.

FIG. 2 is a detailed view in cross-section of a channel with an electrode.

FIG. 3 is a top plan view of the bottom substrate.

FIG. 4 is a top plan view of the top substrate.

DETAILED DESCRIPTION

Figure 5:
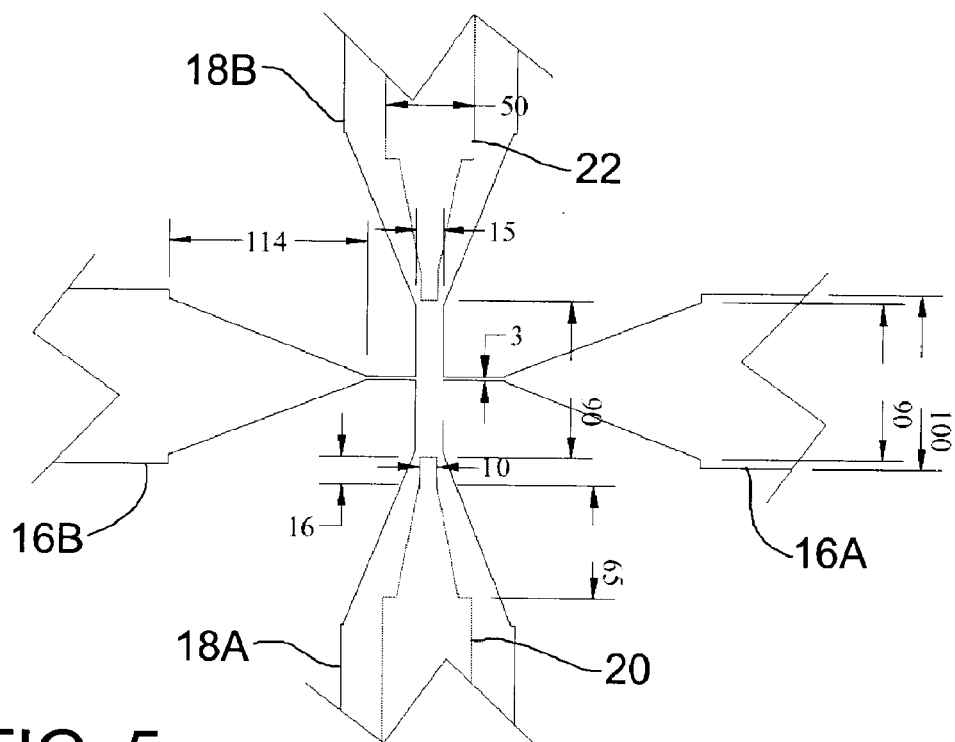
FIG. 5 is a detailed view of the intersection of the channels with dimensions in micrometers.

The techniques described herein use an electric field to destabilize a thin film established at a common point between channels in a microfluidic substrate. Application of an electric potential difference across the thin film causes a modification of the film, eventually resulting in a break up of the film if sufficiently large potential differences are applied. The target droplet sizes (and hence, the film radius of curvature) for the device and procedure described below is generally <5-10 μm. As an example, these techniques may be used for rapid identification of proper de-emulsifiers for micron size emulsion droplets by application of appropriate electrochemical perturbations to the interface of the emulsion droplets. Thus the term micro in relation to a channel or microfluidic device is a channel or device whose functional features, such as the cross-sectional dimensions of a channel, are less than 50 microns in length, and preferably less than 10 or even 5 microns for example for the study of oil droplets in water. The channels need not be perpendicular to each other, but need to be sufficiently distinct from each other to allow a thin film to form. In addition, stability requirements may require control features in the chip, such as pumps, valves and channel configuration to ensure stability of the thin film.

The platform described below is a microfluidic chip with intersecting channels, where one channel is filled with a liquid capable of forming a thin film between the other liquid or liquids in the other channel. The embodiment and results described below are directed toward oil and water as this is useful in finding a suitable de-emulsifier for the petroleum industry. However, those skilled in the art will recognize that the teachings may be applied to other immiscible fluids, or fluids capable of forming a film. In one embodiment, two electrodes are deposited at the bottom of the water channels using photolithographic methods. These electrodes are utilized to apply the electrical field required to rupture the film, as well as for measuring the critical voltage at which the break up occurs.

Microfabrication of the Electrochemical Detection Platform

When two water droplets approach each other in an oily medium, they need to break the thin film of oil between them in order to coalesce. This film of oil can be fairly stable and difficult to rupture. Surfactants are added to the emulsion to reduce the interfacial forces in oil sand extraction processes. Due to the variable nature of the oil-sand and complex composition of bitumen, the best suited surfactant for every batch of oil sand has to be determined using complicated experiments. The microfluidic chip described herein may be used to study coalescence of water droplets in different types of oil media in the presence of different surfactants. The microfluidic chip is preferably designed in order to be able to emulate emulsion droplets that occur in practice, for example, in a range less than 10 μm. This chip with embedded electrodes at the bottom of the channel can help the user understand the behavior of the thin film of oil between two water droplets approaching each other. It has been found that such films can be formed at the intersection of two microchannels, and that a microfluidic chip with these microchannels may be designed with embedded electrodes that allows electrochemical actuation and detection capabilities. To facilitate reproducible performance, the design of the microchip is such that large pressure drops are prevented from developing across the uniform cross-section channels, and a relatively stable thin film is provided at the intersection of the channels. There will be given below a description of a suitable microfluidic chip, the steps to manufacture it, and some preliminary results obtained in using this chip.

Microfluidic Chip Design and Fabrication

Figure 6:
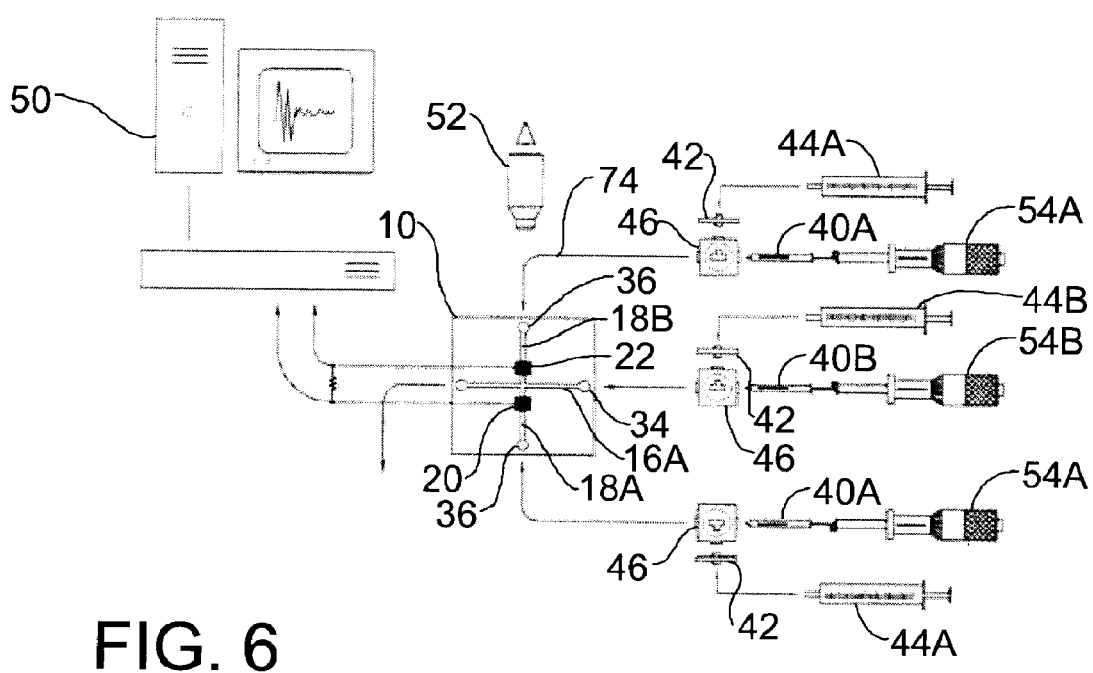
FIG. 6 is an exploded, schematic view of the experimental platform for assessing performance of the microfluidic chip.

Referring to FIG. 2, an embodiment of a microfluidic device includes two substrates: a bottom substrate 12 and a top substrate 14 that are used to form microfluidic channels. It has been found that etching techniques may be used on glass substrates to create suitable channels. As shown in FIG. 1, the bottom substrate 12 has two intersecting channels 16 and 18. Channel 18 has electrodes 20 and 22 on each side of channel 16. While channels 16 and 18 are shown to be perpendicular to each other, this need not be the case in all designs. Other angles are possible, as long as the channels 16 and 18 are sufficiently distinct from each other to allow a thin film to form. Referring to FIG. 2, top substrate 14 acts as a cover. Referring to FIGS. 3 and 4, top substrate 14 provides the access to the channels 16 and 18 through four drilled wells 24, 26, 28, and 30. While glass may be used to form these substrates, those skilled in the art will understand that other materials that can be etched or otherwise manipulated to form intersecting channels may also be used. For example, other embodiments may be formed from polydimethylsiloxane (PDMS), or a combination of materials, using steps that are known in the art of manufacturing microfluidic chips. The horizontal channel 16 delivers the liquid that makes the film, such as a hydrocarbon with some added surfactants. Channel 16 divides the vertical channel 18 into two halves, each half delivering the other liquids. In the experiments described below, liquids such as an aqueous sodium chloride or potassium chloride solution in both halves are used that flank the thin film formed of an oil mixture. The liquids in the two halves of the vertical channel 18 can be different or the same, and represent two droplets that are separated by a thin liquid film. The drain 32 of the system is located at the opposite side of the horizontal channel's input 34. This is where all liquids drain out. The vertical channel 18 has two inputs 36 and 38 at opposite ends. Referring to FIG. 1, drain 32 and inputs 34, 36 and 38 in bottom substrate 12 correspond to wells 24, 26, 28, and 30 in top substrate 14, respectfully. Referring to FIG. 6, once assembled, channel 16 forms an oil channel 16A with input 34 and a drain channel 16B with a drain 32, while channel 18 forms two water channels 18A and 18B, with inputs 36 and 38, respectively.

Figure 14:
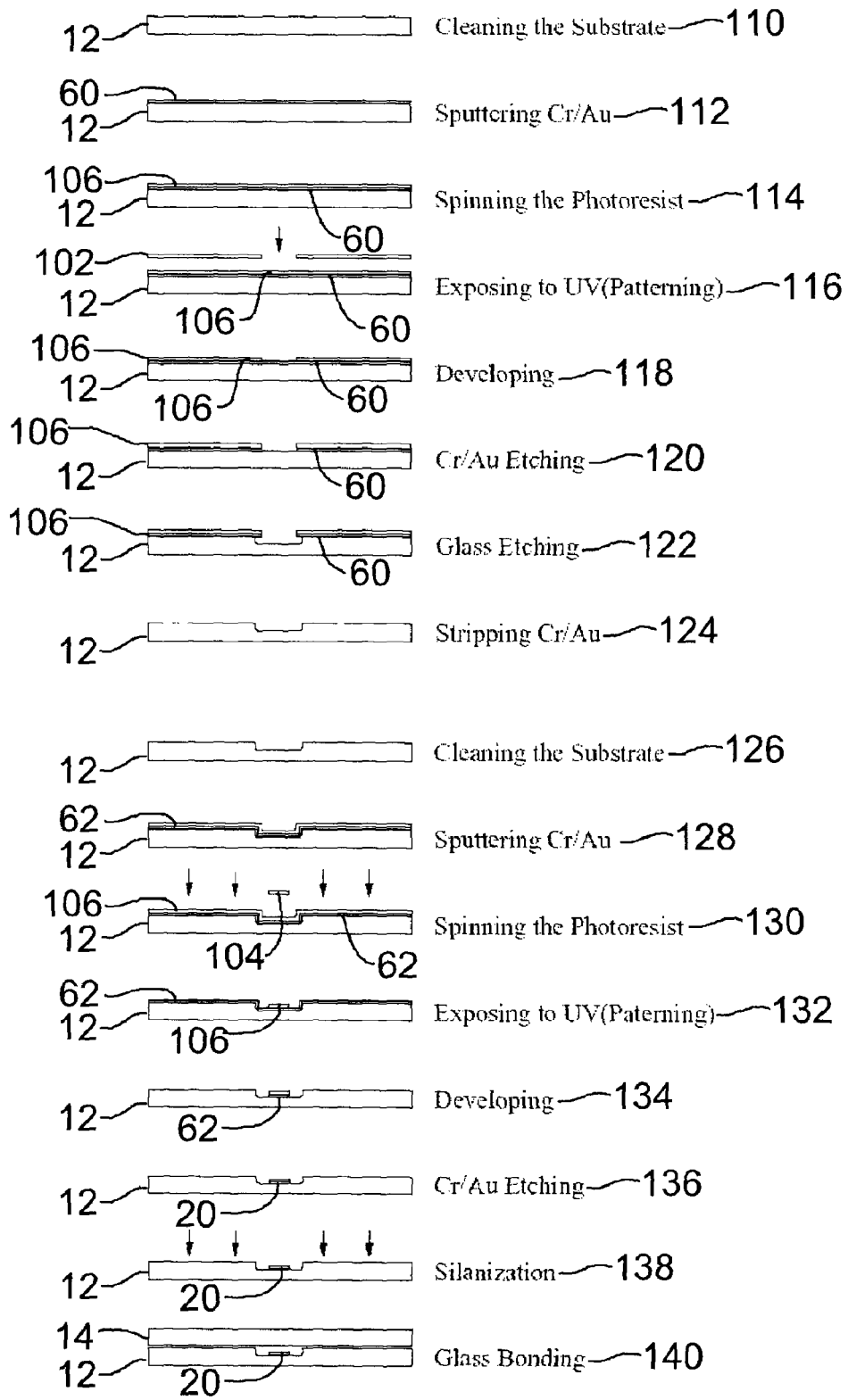
FIG. 14 is a cross-sectional view of the steps of the microfabrication process.

FIG. 3 depicts the general design of the bottom substrate 12 and FIG. 4 depicts the general design of the top substrate 14 making an embodiment of the microfluidic chip. The microfluidic chip used in the experiments described below used substrates made of Borofloat™ glass with 1.1 mm thickness. The top substrate fabrication involved drilling four ports. The bottom substrate design is more complex, involving fabrication of the channels as well as deposition of metal electrodes. An embodiment of fabrication steps are shown in FIG. 14, with a more detailed description of the steps given at the end of this document. The channels 16 and 18 (only channel 16 is depicted) are for example etched into the bottom substrate 12 using standard etching process with hydrofluoric acid. Except the channel lines, the substrate is covered with a thin layer 60 of Cr/Au, following which it is immersed in a hydrofluoric acid solution. This results in dissolution of the glass at the exposed areas and formation of the channels 16. The depth and the size of the channels are controlled both by the mask design and the etch depth.

FIG. 5 depicts a detailed design of the masks for the bottom substrate 12 at the intersection of channels 16A, 16B, 18A and 18B. While the actual size of the channels may vary depending on the ultimate use and preferences of the user, the dimensions shown, in microns, are an example of a design that performed adequately. The results presented in this report pertain to channels with 8.5 µm depth and 30 µm width at the intersection. In order to reduce the pressure drop, the microchannels were designed to have a tapered shape, with a significantly wider cross section (for example, 125 µm) as one recedes from the intersection zone. The oil channel 16A was silanized to make it hydrophobic in order to prevent the water from entering this channel, and to prevent current leakage through the thin layer of water at the intersection. Channel 16A and 16B have to be hydrophilic, in this example, thus there is no modification required to the surface if glass is used.

The width of the oil channel 16A was designed to be narrower than that of the water channels 18A and 18B. This design of the channels facilitates the process of creating a stable film by providing a large contact area for the two interfaces. Generally, the ratio of the water to oil channel width is controlled by two factors. The first factor is the mask design. The width ratio of the mask in this design is 5:1 (15 µm:3 µm). However, the etching process, which is isotropic, creates a second factor, namely that the etchant penetrates underneath the covering layer (Cr/Au) due to undercutting, thereby rendering the final aspect ratio to be 3:2 for the design depth of 8.5 µm (30 µm 20 µm).

Figure 7:
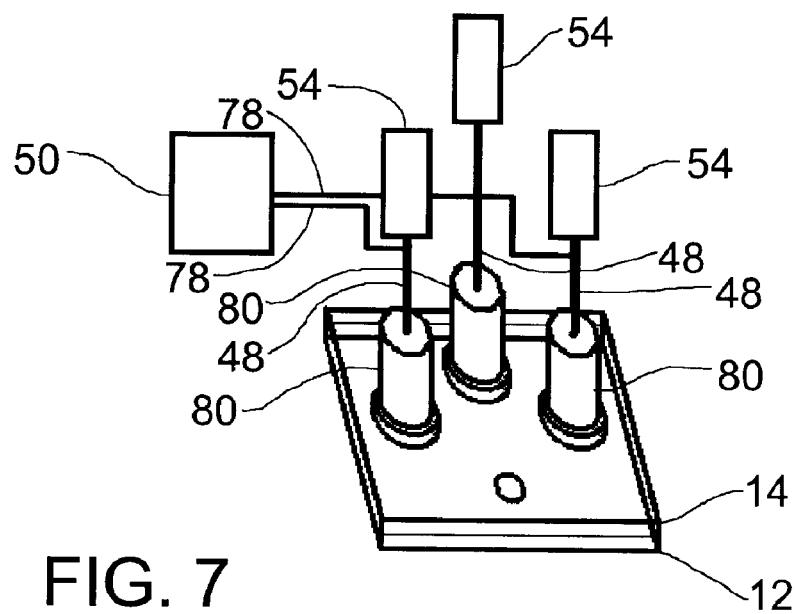
FIG. 7 is a simplified perspective view of the experimental platform.
Figure 8:
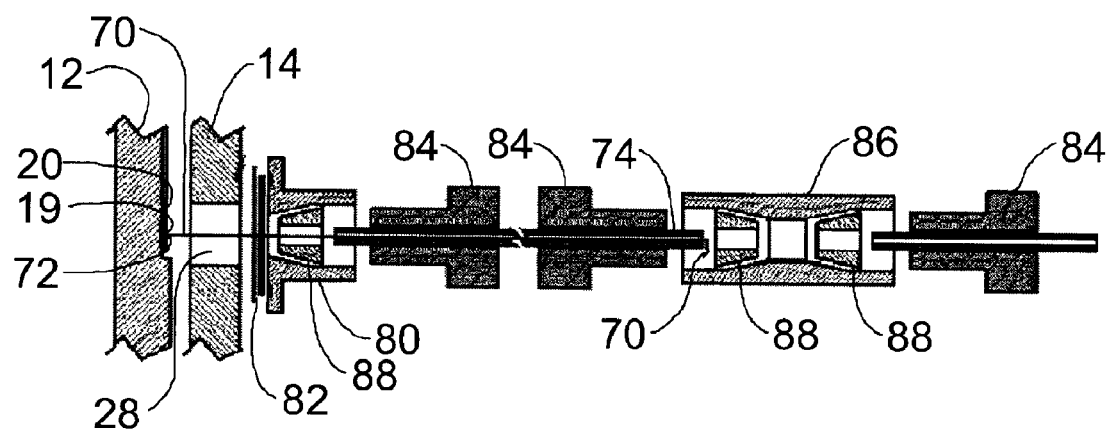
FIG. 8 is a detailed cross-sectional view of the connection assembly used.

Referring again to FIG. 14, the embedded electrodes in the water channels may be deposited by using a sputtering technique in vacuum. First, a 400 nm thick chromium film 62 is deposited as the adhesion layer followed by a 1 µm gold layer. In this design, referring to FIG. 5, electrodes 20 run parallel to the water channels 18A and 18B along their entire length. The width of the electrodes is 50 µm, except near the channel intersection, where they taper down to a width of 15 µm. It has been found that this electrode size would provide a sufficiently strong and reliable signal as well as good conductivity. Referring to FIG. 3, at the end of each water channel 18A and 18B there is a 1 mm diameter circular electrode pad 19 and 21, respectively, which serves as the junction between the electrodes 20 and 22 inside the chip and the measurement device. Referring to FIG. 8, the connection to a stainless steel wire 70 is made using conductive glue 72 (such as Epoxy CW2400 from CircuitWorks). The wires 70 are connected to the stainless steel pipes 74, which, referring to FIG. 7, pass the electrical signal to the measurement instrument 76 through electrical connections 78. Referring to FIG. 5, the distance between the two electrodes 20 and 22 is about 100 µm in this design. Some measurements have indicated that the critical voltage is not very sensitive to the distance between the two electrodes for the channel dimensions of the cell.

Referring to FIG. 8, the connections to the electrodes and channels are both made through stainless steel pipes 74. A Nanoport™ assembly (N-333 from Upchurch Scientific) is attached to the top substrate 14 which provides the connection to channels 16A, 18A, and 18B, with channel 18A depicted as an example. The connecting wires 70 pass through pipe 74 to connect to electrodes 20 and 22 with electrode 20 shown as the example, and are made of stainless steel with a diameter of 50 µm.

The top and bottom substrates 12 and 14 are bonded using conventional glass bonding methods. The substrates 12 and 14 are thoroughly cleaned to ensure that they are free of any contaminations and particles. The substrates are then aligned and pressed against each other. The primary bonding can be made permanent using a heat treatment process at 500° C. FIG. 7 shows a perspective view of the final product. The sequential steps involved in one embodiment of a microfabrication process are outlined at the end of this patent document.

Experimental Test Platform, Materials and Methods

FIG. 6 depicts a schematic diagram of the experimental setup developed to test the performance of an embodiment of a microfluidic chip. The setup includes the microfluidic chip 10, manual microsyringe pumps 40A (for the electrolyte solution) and 40B (for the oil solution) for fluid delivery and control of the film, filters 42, reservoirs 44A for the electrolyte solution and 44B for the oil solution, switching valves 46, tubes 74, electrical connections 20 and 22 and the measurement and data acquisition system 50, such as a potentiostat that both applies a potential and that measures current through the apparatus. The microfluidic chip may also be placed on an inverted optical microscope 52 for visual feedback on the film breakup. Using this design, electrodes 20 and 22 in combination with measurement and data acquisition system 50 allow the user to simultaneously apply an electric potential and measure the conductance/impedance of the thin film. In other words, both actuation and detection are achieved on a single platform.

In the embodiment depicted, three manual syringe pumps were used: two for the electrolyte solution labeled 54A and one for the oil phase labeled 54B. In other embodiments, different delivery methods may also be used, such as electroosmotic flow. Using a micrometer head, the manual microsyringe pumps 40A and 40B are employed to inject the fluid to the system. The fine resolution of the micrometer screws (less than a micron pitch), helps to retain an accurate control over the fluid injected to the system. The accuracy of the control over the injected fluid is an issue of immense concern, as the success of the measurement depends greatly upon the capability of the system to maintain a very accurate control over the two oil/water interfaces.

Due to small cross section of the channels at their intersection, and need for accurate control of the interface within a few micrometers, it is necessary to prevent any expansion or contraction of the system elements (particularly the tubing) due to applied pressure. This may be accomplished for example by using high strength components in all parts of the system. The tubing and connections used in the experiments are all PEEK™ with 1/16" and 0.01" outside and inside diameters, respectively. In order to avoid any clogging inside the chip, fine filters 42 (from Sartorius) with 0.2 μm pores have been used between the reservoir 44 and T-valves 46. Since the volume of the microsyringes 40A and 40B is small and the microsyringe pumps 54 have a limited stroke, it is necessary to have a reservoir 44 at the input of each line 74 so that when ever the syringe runs out of liquid, it can be refilled from the reservoir. The T-valves 46 (3-way flow switching valve V-100T from Upchurch Scientific) have been used to close the chip's input and connect the microsyringe to the reservoir in order to refill the syringe 44. The T-valve 46 connects two of its input/outputs at each valve position.

The connections of the pipes to the chip were made using Nanoport™ assemblies 80 (Upchurch) as shown in FIG. 8. These connections were chosen as they provide the access to the input well of the chip with a minimum dead volume. They are glued to the surface of the top substrate using an adhesive 82 provided by the manufacturer that ensures proper bonding of the Nanoport™ material to the glass substrate 14. Other components used in this connection include nuts 84, an adapter 86 and ferrules 88.

Referring to FIG. 6, data acquisition system 50 was a Voltalab™ system with Voltamaster™ software (from Radiometer Analytical) to be used as power supply, data acquisition and measurement instrument in the experiments. Voltalab™ was chosen as it is a dynamic laboratory electrometer that can apply DC potential up to 15V. It measures the potential and current with resolution of 60 μV and 30 pA, respectively. It is also capable of impedance spectroscopy up to maximum frequency of 100 kHz.

Aqueous Solutions and Oil Samples for the Film

In the preliminary experiments, the oil phase was prepared by diluting bitumen at different concentrations in a 50/50 (v/v) mixture of heptane (HPLC grade H350-4 from Fisher Scientific) and toluene (HPLC grade T290-4 from Fisher Scientific). This mixture will be referred to as 50/50 Heptol henceforth. The concentration of bitumen in 50/50 Heptol was varied from 0.3% to 30%. This mixture is known to result in fairly stable thin films depending on the concentration of bitumen. The electrolyte used in these experiments is 1% aqueous solution of sodium chloride.

Procedure of Creating the Film

Speaking generally, the film compression process includes two steps: first a gradual compression of the film using fluid pressure to an ultra-thin state, followed by the use of a ramped voltage across the ultra-thin film to break it. This procedure is necessary for the films formed between microscopic droplets. In the confinement of microchannels, films can be inherently unstable owing to the enormous capillary pressures with which the water columns compress the oil film. The chip design of one embodiment was designed with tapered channels, such that, when combined with the controlled pressure application, the destabilizing effects of the capillary pressure on the film drainage was removed. This allowed the formation of a "stable" ultra-thin film before application of electric potential. While the drawings show the tapered section connected to a straight section before the intersection, in some embodiments the taper may continue to the intersection. The oil and drain channels 16A and 16B may also tapered to provide more control over the fluid pressure in those channels. After this, the electric potential is applied as a ramp, and the film is gradually perturbed, which leads to a very accurate and reproducible detection of film stability. If instead, one applied a step input potential difference across an initially thick film, the film would spontaneously break under the combined influence of capillary pressure and electric field. This would make obtaining any meaningful correlation between the applied voltage and the film rupture point virtually impossible. These steps are described in more detail below.

Referring to FIG. 6, the first step in creating the film is to flush the air out of all the components connected to the chip including tubes 74, valves 46, etc. Once all of the tubes 74 are filled with the appropriate liquids, they can be connected to the input connectors as shown in FIG. 8. The next step in this example is to flush out any air trapped inside microchannels 16A, 16B, 18A and 18B. This may be done using water, which is injected into the channels to displace all air.

Referring to FIG. 6, once all the channels are filled with water, oil can be injected slowly into channel 16A. It is important to create a pressure higher than that of the pressure inside the chip to create a uniform flow from all three channels to the drain channel 16B, which prevents liquids penetrating any other channel. This can be done for example using the manual pumps 54 and watching the flow under the microscope 52. While using microsyringe pumps 54 is a relatively inexpensive and convenient method of fluid delivery, other methods may also be used to achieve desired results, such as electroosmotic flow. In this embodiment, it usually takes 20-30 minutes for the system to equilibrate. The equilibrium condition includes both temperature equilibrium with environment and the pressure equilibrium of all channels. During the equilibration stage, it is important to watch the system closely under the microscope 52 and keep the pressure inside each channel 16A, 18A and 18B equal by controlling the flow. Once the chip has been calibrated, the microscope 52 is no longer necessary.

Once the system reaches the equilibrium and there is no flow in the channels, from this point on, it is very important in the particular embodiment shown to pump the fluids very gently with steps of less than a micron. The two oil-water interfaces can be drawn towards each other either by pushing the water syringes 44A in or pulling the oil syringe 44B out. Once the two interfaces touch each other, the film is formed. At this point, the control of the syringes is very important to keep the film stable. The life time of the film can be measured after the two interfaces come in contact till they disintegrate.

Figure 9A:
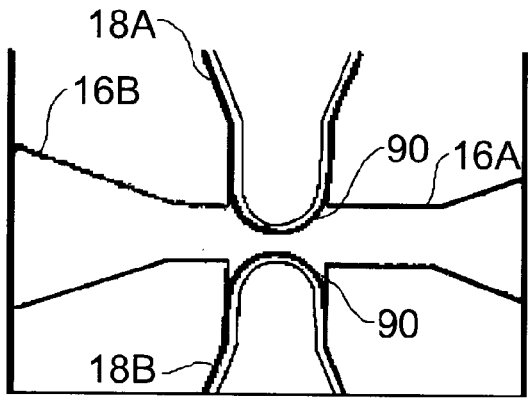
FIGS. 9A through 9F show the procedure of creating a thin film.
Figure 9B:
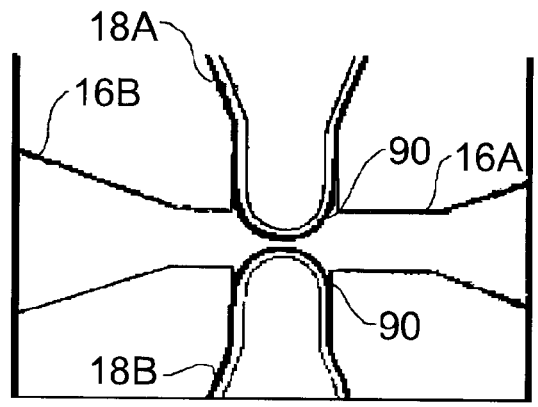
Figure 9C:
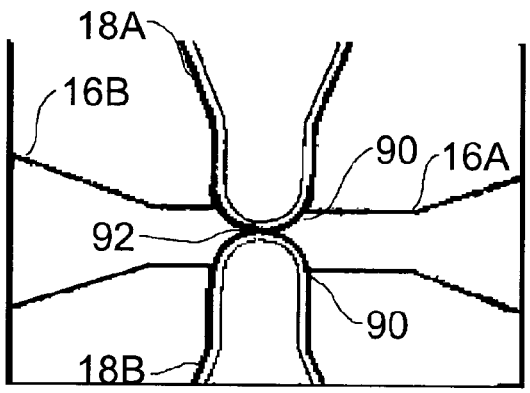
Figure 9D:
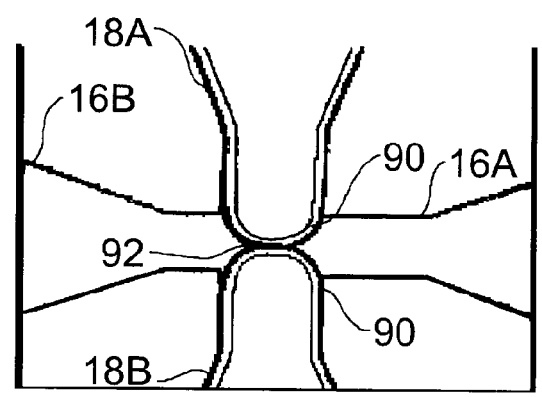
Figure 9E:
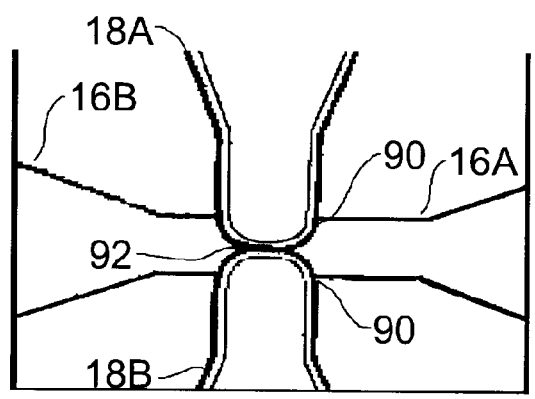
Figure 9F:
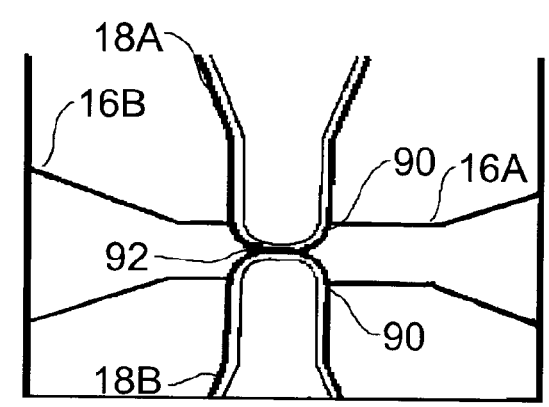

FIGS. 9A-9F demonstrate the procedure of creating the thin film. The two water phases 90 are located in channels 18A and 18B. In the example from which the images were taken, the width of the water and oil channels was 30 μm and 20 μm, respectively and the depth of the channels was 8.5 μm. The oil was 3.16% diluted bitumen in 50/50 Heptol and the electrolyte was 1% aqueous solution of sodium chloride. By adjusting the microsyringe pumps, the water columns 90 are pushed against each other from the position in FIG. 9A to the position shown in FIG. 9B, and eventually pinching the thin oil film 92 in between as shown in FIG. 9C. If the film 92 is stable, increasing the water column pressure as shown in FIG. 9D through 9F results in compression (thinning) and flattening of the film 92. Higher pressures can eventually lead to rupture of the oil film 92.

FIG. 1 shows the location of the electrodes 20 and 22 in water channels 18A and 18B, as well as the shape and size of the thin film relative to the overall chip dimensions. It should be noted that the formation of the film 92 does not involve the electrodes 20 and 22. The film formation is effected by direct manipulation of the pressure in the channels using the microsyringe pumps 44A and 44B as shown in FIG. 6. However, once the film 82 is created, the electrodes 20 and 22 play a critical role in establishing an electrical field across it, and measuring the electrical properties of the film 92.

Breaking the Film

DC Potential Measurement and Critical Voltage

Figure 10:
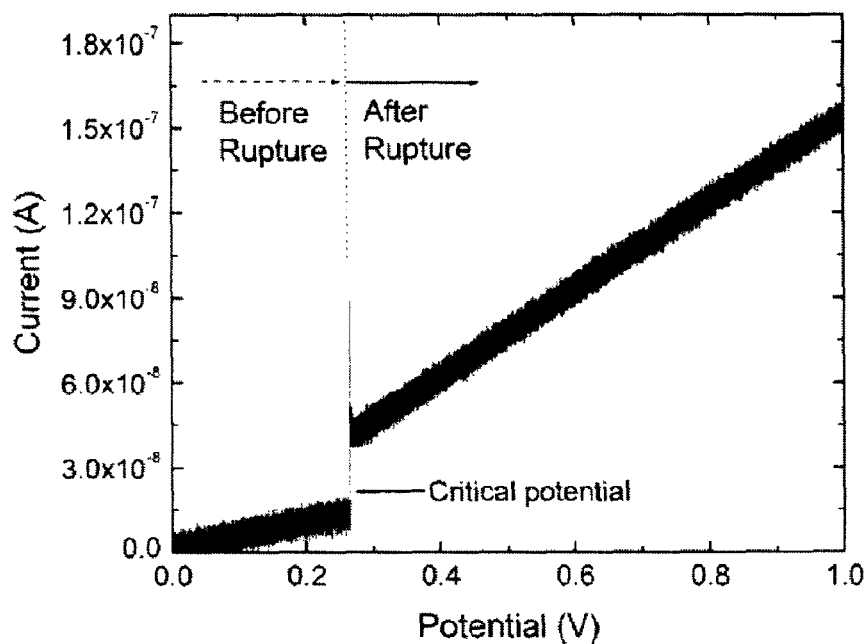
FIG. 10 is a graph showing the current potential characteristics of thin film breakup experiments using 3.6% bitumen in 50/50 Heptol film.

Referring to FIG. 10, when the two water droplets 90 are coalesced (that is, the oil film is absent) and make a continuous connection between the two electrodes 20 and 22, the voltage/current curve of the system demonstrates a fairly linear behavior in the voltage ranges studied here (0-1V) which depicts a constant resistance of the electrolyte. While the film 92 exists, it insulates the electrical connections between the two electrodes 20 and 22 through the electrolytes and there will be a large resistance in the system. This difference in the measured resistance in presence and absence of the film 92 can be used to distinguish the presence or rupture of the film 92. When the oil film 92 separates the two water columns 90 in channels 18A and 18B, application of a DC potential across the film results in a polarization of the two oil-water interfaces. The migration of ions (in the aqueous phase) to the interface would modify the electrical field across the film 92, and consequently, the Maxwell stresses help cause the break up of the film 92. This break up voltage, which will be termed the critical voltage, depends on several parameters, including the interfacial properties of the liquids involved, concentration of bitumen in the Heptol, temperature, adsorption time, etc.

Once the film 92 is formed, a ramp DC potential is applied on the electrodes 20 and 22 by the data acquisition system 50 shown in FIG. 6. At the critical voltage, the film 92 will be broken and a processor such as a potentiostat (Voltalab™ 80, Radiometer Analytical, USA) records the critical potential at the time of rupture.

Impedance Spectroscopy

Impedance spectroscopy may also be used to investigate interfaces. The general idea is to apply an AC signal with a known frequency and amplitude and measure the response of the system to the original signal using the data acquisition system 50. The response of the system would reveal the impedance and the phase shift from the original signal. Using this technique, one can measure the capacitance and conductance of the system. The capacitance of the film 92 can be correlated to the thickness of the film 92. It can also be used to measure the thinning rate of the film 92. The behavior of the system with regards to the applied signal reveals the equivalent electrical circuit of the system. The outcome of the impedance spectrometry can be represented in a Nyquist diagram. The horizontal axis in the Nyquist diagram shows the real part of the impedance while the vertical axis plots the imaginary part. Each point on the Nyquist plot represents the impedance vector corresponding to a different frequency.

Experimental Results

Voltage/Current Characteristics:

Preliminary experiments with the microfluidic chips were conducted with a 3.16% bitumen in 50/50 Heptol oil phase as the film forming system, and the setup described above. Referring to FIG. 1, once the film is formed by bringing the water columns 90 in contact, a ramped DC signal is applied to the electrodes through the potentiostat Voltalab™ instrument 50 shown in FIG. 6. The current was measured using the same electrodes 20 and 22 used to apply the signal. FIG. 10 depicts the current/potential behavior of the system after application of a ramped DC potential. Initially, at low applied voltages the graph demonstrates a linear increase of the current with a smaller slope. The resistance of the system is equivalent to 20 MΩ, which is due to the parallel resistor connected to the circuit. The resistor also helps to stabilize the film The resistor used ought to have a large resistance, such as 5 MΩ or greater. This implies that the resistance of the film is infinitely large or the film is not conductive and the two water droplets 90 are separated. The presence of the film was also verified through direct observation employing the microscope shown in FIG. 6.

As the voltage is ramped up, the electrical field across the film increases. In some embodiments, adequate results have been obtained by ramping the voltage at a rate of 25 mV/s. A suitable ramp may be easily determined for each embodiment in which a ramp is required. The net Maxwell force applied on the surfaces of the film overcomes the inherent disjoining pressure forces, eventually leading to the break up of the film. The break up of the film is manifested by the sharp spike on the current/potential figure. The corresponding voltage is the critical voltage for the film rupture. After coalescence of the water phases 90, the current passing through the system increases due to electrolyte connection parallel to the resistor. This results in a larger slope of the current/potential graph. Thus, the microfluidic chip provides a measurable sequence of signals that allow a clear demarcation between the presence and absence of the oil film. The spike in the current/potential graph and the discontinuity in the resistance (slope of the graph) clearly indicate the critical applied voltage at which the film ruptures. This critical voltage will provide a measure of the stability of the film.

Figure 11:
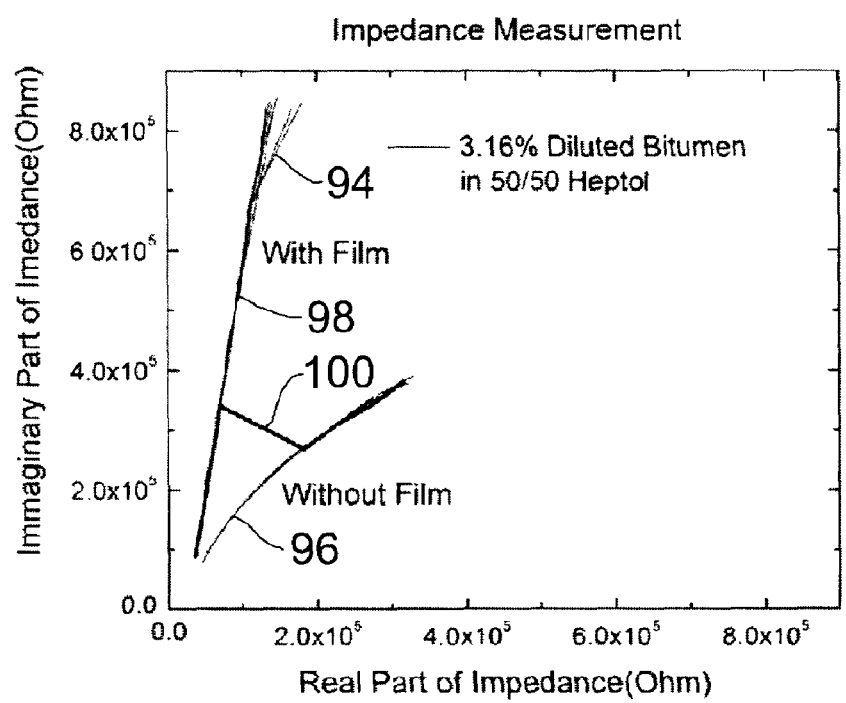
FIG. 11 is a graph showing typical results from impedance spectroscopy experiments.

Impedance Spectroscopy:

Impedance spectroscopy was also performed for the system by applying an AC signal with an amplitude of 10 mV and a frequency range of 1-100 kHz. The real and imaginary components of the impedance are then plotted in a Nyquist diagram. The circuit behaviour differs considerably in presence and absence of the oil film. In absence of the oil film, the frequency response of the system is characteristic of a largely resistive circuit, resembling a curved line (arc of a circle) on the Nyquist plot. In presence of the film, which acts as a capacitor, the Nyquist plot assumes a different slope. The Nyquist plot of the microfluidic chip using diluted bitumen in Heptol for the oil phase and aqueous NaCl is shown in FIG. 11. The graph demonstrates two types of curves. The ones with the greater slope were obtained when the oil film is present. The second set of curves with a lower slope corresponds to the impedance measurement across the aqueous NaCl solution (when the film is absent). Several such measurements were conducted to ensure that the Nyquist plots of these two systems are distinguishable. These measurements are represented as thin lines in FIG. 11, where lines 94 represent the capacitative measurements, and lines 96 represent the resistive measurements. In another experiment, we superimposed the AC signal over a DC ramp. The result of this experiment is depicted in FIG. 11 as the thick line 98. Here, as long as the film is intact, the Nyquist plot follows the characteristic behaviour of the capacitative circuit (with higher slope). The breakup of the film is represented by the jump by line 100 from the capacitative line 94 to the resistive line 96, following which the Nyquist plot represents the behaviour of the system without a film. Using this information, one can calculate the capacitance of the film and its correlation with the film thickness.

The above preliminary results clearly demonstrate the capability of the designed microfluidic chip as well as the experimental setup to determine the stability of thin liquid films. The film can be ruptured with a very low DC potential and the rupture can be detected both with conductivity and impedance measurements.

Figure 12:
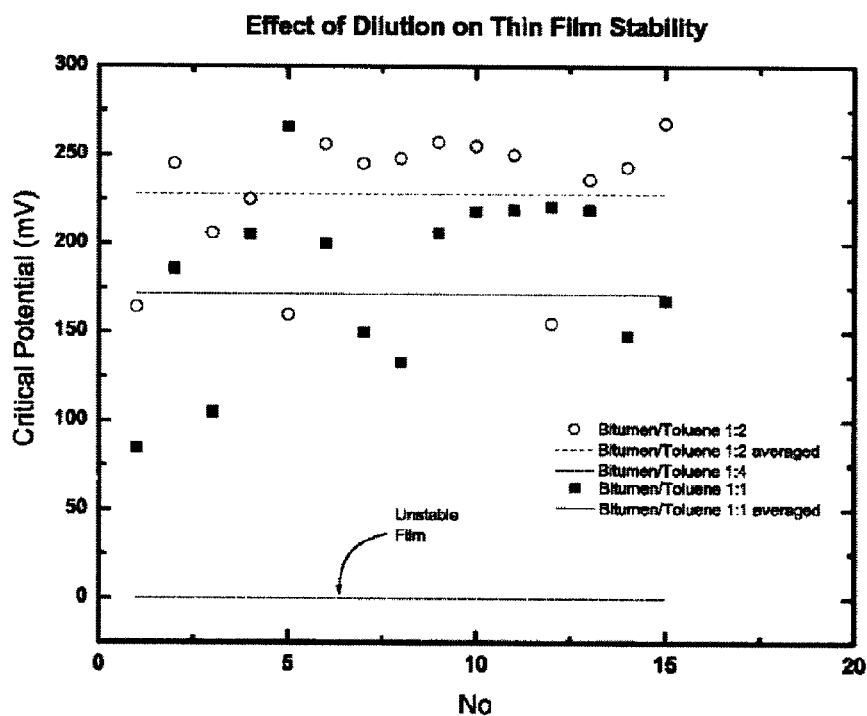
FIG. 12 is a graph showing critical potential for 3 different dilution of bitumen in toluene (1:1, 1:2 and 1:4).

DC Potential Measurement and Critical Voltage:

In order to investigate the sensitivity of the critical potential measured by the chip with respect to the stability of the film two series of experiments have been performed. The material used is diluted bitumen in toluene with two different concentrations. The dilution was changed from 1:1 to 1:4 (bitumen/toluene). The results are depicted in FIG. 12. At dilution 1:1 the average measured break up potential (critical potential) was 170 mV whereas in 1:2 the average was 225 mV. At dilution 1:4, the film was completely unstable. These results are in qualitative agreement with critical disjoining pressure from measurements in K. Khristov, S. D. Taylor, J. Czarnecki, and J. Masliyah, *Colloids Surf A Physicochem. Eng Asp.*, 174, 183, 2000 and S. D. Taylor, J. Czarnecki, and J. Masliyah, *J. Colloid Interface Sci.*, 252, 149, 2002. In those measurements the critical disjoining pressure of the 1:2 solution is higher than that of 1:1. Furthermore, it was reported in the same reference that at dilutions more than 1:3 the film becomes unstable which is the case in the 1:4 dilution.

Figure 13:
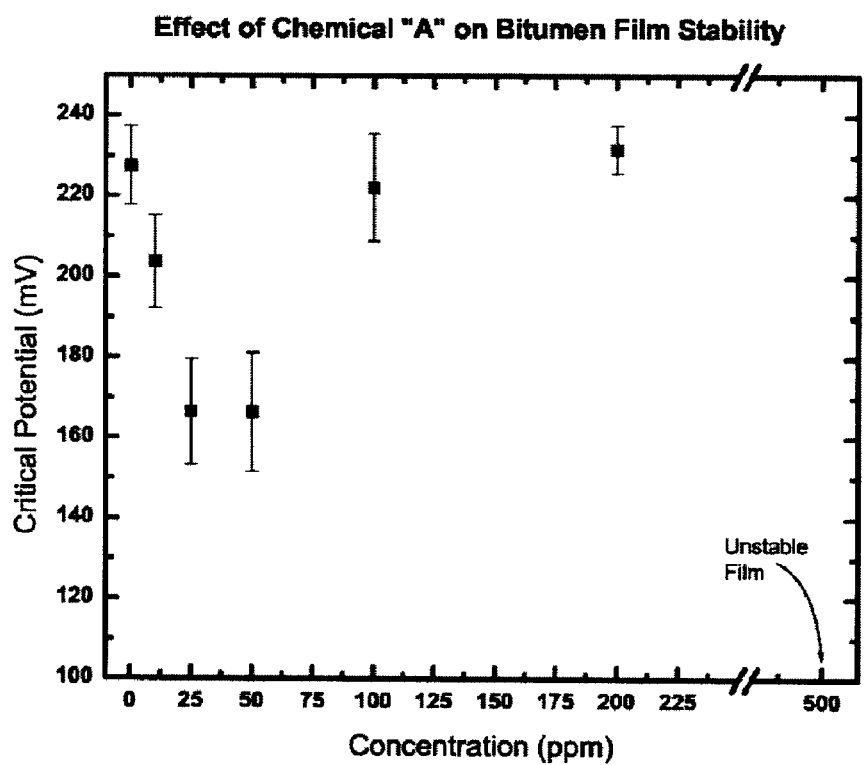
FIG. 13 is a graph of the average critical potential vs. concentration of surfactant "A". The minimum occurs at 50 ppm which is the actual concentration used in industry. At 500 ppm the film was unstable so the critical potential is zero.

The second experiment of this kind is a study on the effect of a surfactant on stability of the film. A proprietary surfactant of Champion Technologies was used as flocculating agent. Henceforth it will be called surfactant "A". The results of critical potential vs. concentration of the chemical in a solution of bitumen/toluene 1:2 are depicted in FIG. 13. The results show a decline of the film stability at low surfactant "A" concentration. The stability of the film reaches a minimum at 50 ppm and then it increases again. At higher concentration (up to 200 ppm) it seems to be constant while at concentrations of about 500 ppm, it becomes completely unstable. Unfortunately there are no quantitative results for this surfactant to compare with, but results match the available qualitative information very well. The optimum concentration for this chemical at Syncrude's plant is 50-55 ppm and it has been observed that by overdosing the chemical the emulsion becomes more stable.

Toluene and Lecithin Mixture

Another set of measurements was taken using a similar setup to the one described above. The oil phase was toluene (HPLC grade, Fisher Scientific, USA) containing soybean lecithin (L-α-lecithin, Calbiochem, USA) as surfactant. The oil film was formed between two aqueous electrolyte columns, containing 1 wt. % NaCl, at the intersection.

In each experiment, the lecithin molecules were allowed to adsorb for a fixed adsorption time at the oil-water interfaces of the individual droplets before bringing them together to form the film. The two interfaces were then brought together slowly to form the film by adjusting pressure. Once formed, the film was left to drain and attain a stationary state over a period of 1 minute (drainage time) before application of the ramped DC potential. For a given film, the adsorption and drainage times were kept constant in order to achieve consistent and repeatable experiments.

Figure 17:
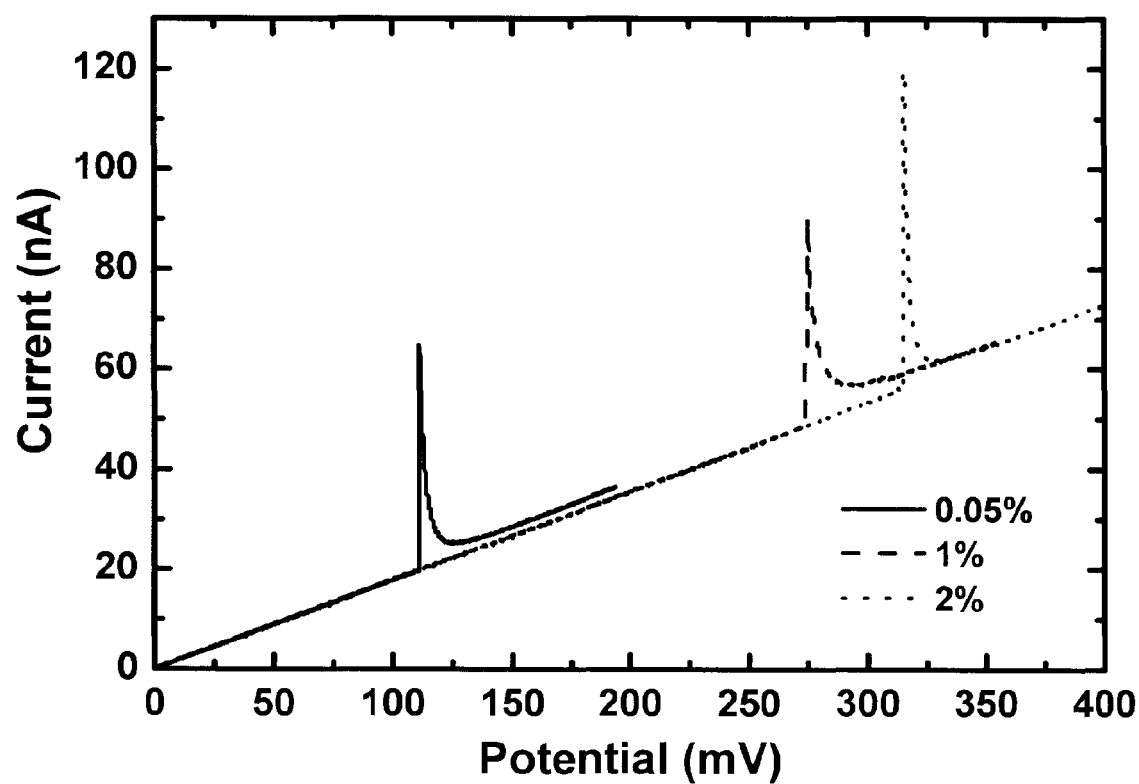
FIG. 17 is a graph depicting the typical conductance behavior of films formed using three different concentrations of lecithin.

FIG. 17 depicts the typical conductance behavior of films formed using three different concentrations of lecithin. When the film is intact (at low potentials), the current linearly increases with the potential, the slope (potential/current) being 5 MΩ. Since the oil film is virtually non-conducting, the measured current predominantly passes through the parallel resistor (5 MΩ). During this stage, the two interfaces of the film, which acts as a capacitor, acquire a charge. Once the potential reaches the critical value, the film ruptures. The breakup of the film results in the discharging of the capacitor, yielding the spike in the current.

Figure 18:
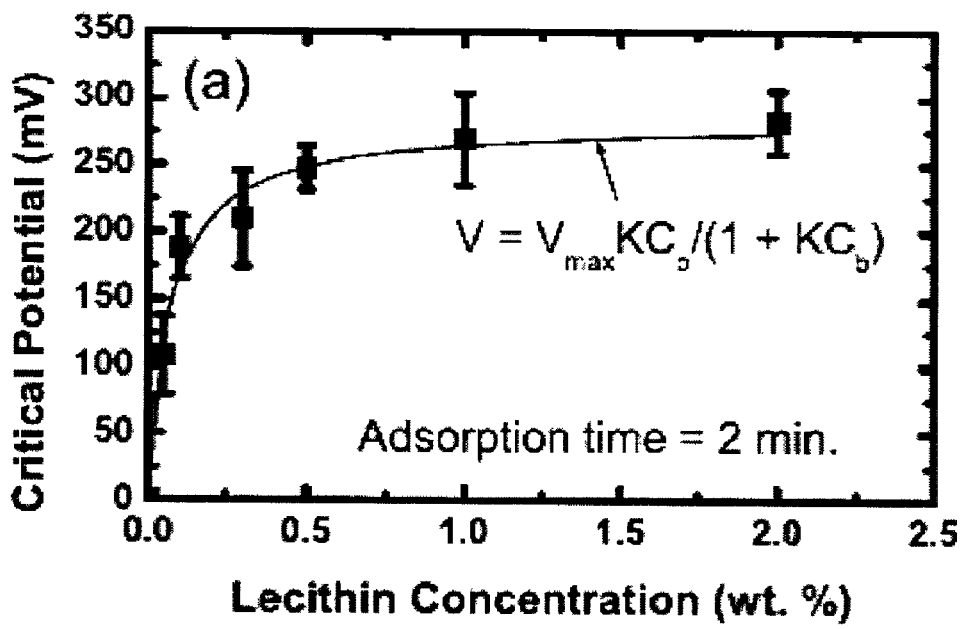
FIG. 18 is a graph of the average critical potential versus the concentration of lecithin.
Figure 19:
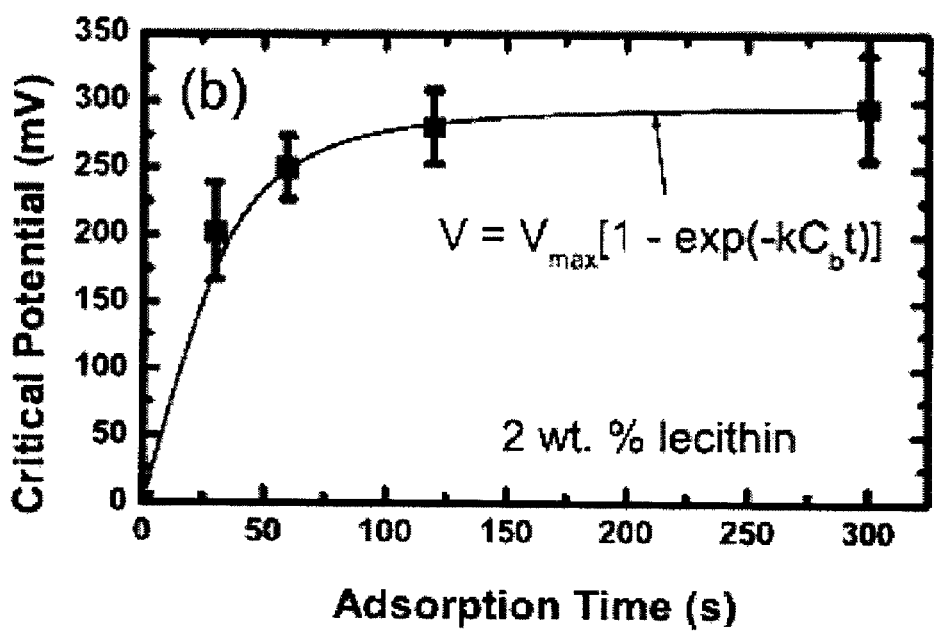
FIG. 19 is a graph depicting the effect of adsorption time on the stability of the thin film.

It is apparent from FIG. 17 that the critical potential is unique to each film formed using a different lecithin concentration. FIGS. 18 and 19 show how this critical potential provides insight regarding the adsorption of lecithin to the oil-water interfaces. FIG. 18 depicts the variation of the critical potential with lecithin bulk concentration in toluene. The data corresponding to each lecithin concentration represent averages and standard deviations calculated over at least 15 measurements. The adsorption time was fixed at 2 minutes in these experiments. FIG. 19 shows variation of critical potential with lecithin adsorption time for a system comprised of 2 wt. % lecithin in toluene. The increase in critical potential with lecithin bulk concentration, as well as with time is representative of the enhanced film stability caused by adsorption of lecithin to the interface.

Using the Langmuir adsorption model, the isotherms and kinetics of adsorption can be expressed as:

$$\frac{\theta}{\theta_{max}} = \frac{KC_b}{1 + KC_b}$$

and $$\frac{\theta}{\theta_{max}} = 1 - \exp(-kC_b t)$$

respectively, where $\theta$ is the fractional lecithin coverage of the oil-water interface, $\theta_{max}$ is the maximum fractional interfacial coverage, K is the equilibrium constant, k is the adsorption rate constant, $C_b$ is the bulk lecithin concentration, and t is the time. If the critical potential is linearly dependent on the film stability, and if stability is directly proportional to the surface coverage, then the data in FIGS. 18 and 19 can be fitted to the isotherm and the rate of surface coverage, respectively, using single adjustable parameters. The solid lines in FIGS. 18 and 19 depict these best fits, normalized with respect to the maximum critical voltage, $V_{max}$. In FIG. 18, the fitting parameter is K, while in FIG. 19, the parameter is k. It is evident that the data are in reasonable agreement with the trends of Langmuir adsorption in both thermodynamic and kinetic aspects.

Although the impact of surfactant concentration and adsorption time on emulsion stability are clearly discernable, electro-coalescence studies involving dynamic systems may miss this adsorption induced stabilization of films due to the hydrodynamic forces in rapidly draining films. FIGS. 18 and 19 depict that even for micron-size droplets, considerable adsorption time is required to achieve a stable surfactant coverage of an interface. By maintaining the stationary condition in the channels before application of the ramped potential, extremely stable lecithin films are formed in our system. This mitigates the hydrodynamic drainage of the films when the additional electrical stresses are imposed, and we recover a situation where the coalescence of the two interfaces is primarily due to electric breakdown of the thin lecithin stabilized oil film.

The experiments reported above were designed to emulate films with average radii of curvature ca. 6.5 μm. By forming an initially stationary film and maintaining consistent adsorption and drainage times, it was found that the electro-coalescence was predominantly governed by electric breakdown of the thin liquid film, which minimizes the hydrodynamic drainage effects on the measured critical potential.

Concluding Remarks

One of the advantages of an embodiment of a microfluidics chip presented in this report is its capability of reducing the film area by 1 to 2 orders of magnitude with respect to other methods, such as the TLF apparatus which has a film diameter of ~100 μm and the micropipette experiment where the diameter of the pipettes barely reaches less than 20 μm. Using the setup developed and reported here film diameters within the range of 1-10 μm is easily obtained. This size of droplets replicates the actual droplet size encountered in the oil-sand industry. Another benefit of miniaturizing the system is the substantial reduction in the effect of unwanted instabilities occurring during the course of the experiment thereby increasing the reproducibility of the results.

Details of Microfabrication

The details of the microchip fabrication process used to prepare the above device will now be described. Other ways of creating the microfluidic platform may be used, including by boring channels in a solid substrate, or using known techniques for working with PDMS. The method described here is a convenient way to carry out the fabrication. This process example has 3 major steps:

Sputtering: Covering the substrate with a thin layer of metal.

Patterning: Transferring the desired pattern to the substrate.

Etching: Removing unnecessary parts of the substrate or metallic covering layer.

These steps are repeated in a cyclic manner depending on the design requirements. The microfluidic chip in the present design consists of one cycle for glass etching and a second cycle for the electrodes. FIG. 14 shows the various steps involved in the present microfabrication process cycle. Following is a brief description of each process step:

Substrate Material: The material for the substrates 12 of the microfluidic chips are Borofloat glasses from SCHOTT. 0211 glass was also tried out in this study but due to the shallow angle of the channels obtained by etching of this glass, we discontinued its use.

Figure 15:
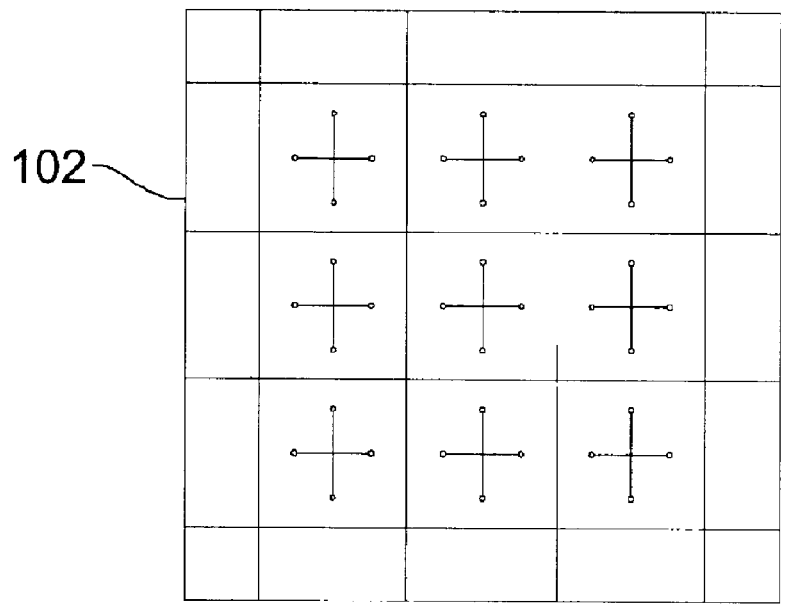
FIG. 15 is a top plan view of the mask designs for the bottom substrate channels.
Figure 16:
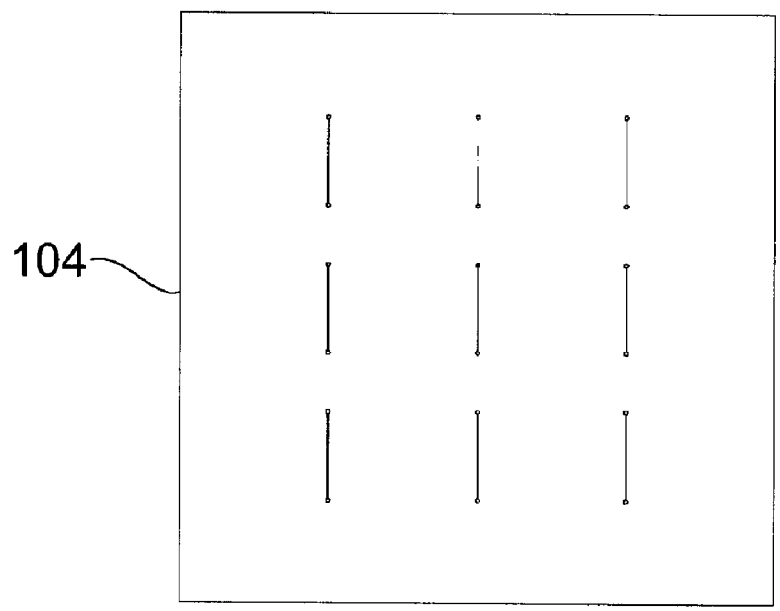
FIG. 16 is a top plan view of the mask designs for the bottom substrate electrodes.

Design and Masks: The masks were designed using L-Edit software. The design includes two different masks for fabricating the bottom substrate 1: one mask 102 is shown in FIG. 15 for channels and another mask 104 is shown in FIG. 16 for electrodes. Each mask includes 9 chips on a 4"×4" square substrate. The size of each chip is about 1"×1". The masks were generated using a Heidelberg DWL-200 laser mask writer.

Cleaning: The substrates were chemically cleaned in step 110 prior to sputtering. Any contamination of the substrate's surface would affect bonding of the sputtered material to the surface. The cleaning is done using a mixture of 25% hydrogen peroxide and 75% sulfuric acid (v/v) (the piranha solution). The mixture produces significant amount of heat which can raise the solution temperature up to 110° C. Substrates 12 are immersed in this solution for at least 15 minutes to ensure that all organic contaminants will be removed. Following immersion in piranha solution, the substrates 12 are washed in DI water and dried. After washing and drying, the substrates are ready for sputtering.

Sputtering: In step 112, a vacuum sputtering system is used to sputter the masking layer 60 over the substrates 12. The first layer is a 30 nm chromium as an adhesion layer (since gold does not bond with glass very well). Following this 150 nm layer of gold was deposited onto the chromium layer.

Spinning the Photoresist: the photoresist 106 is applied in step 114. The photoresist used in this work is HPR 504. It is a low viscosity resist which can be spread over the substrate with a thickness of 1 μm. The spreading speed is 500 rpm for 10 seconds followed by 40 seconds of fast spinning up to 4000 rpm.

Curing: After spinning, the photoresist is dried by baking in a furnace. For glass substrates covered by 1 micron thick HPR 504 resist, 30 minutes curing at 115° C. is recommended. The curing time depends on the type of the resist and the substrate.

Exposure of Photoresist: Once the resist is baked, it is ready for exposure in step 116. AB-M contact mask aligner has been used for the lithography task. The exposure process starts with setting the mask 102 on the mask generator. It is important to make sure that the mask is cleaned before mounting on the machine. Once the mask 102 is mounted, the substrate 12 can be mounted on the substrate holder using a vacuum. After alignment, the substrate 12 can be brought to contact with the mask 102. It is crucial to make sure that the substrate does not move or change its position once it contacts the mask, otherwise the alignment has to be performed again. It is also important to make sure that the mask 102 and the substrate 12 are in good contact. Presence of particles could create a gap between the two and this could let the diffused light penetrate under the mask causing reduced thickness of connections or partial exposure of some parts. The exposure time is generally between 4 to 4.5 seconds.

Developing Photoresist: In step 118, the photoresist is developed. Developing photoresist is a chemical process in which the exposed substrate will be immersed in developer. Developer dissolves the exposed part of the photoresist, leaving the substrate covered with unexposed photoresist. The standard developer for HPR 504 and 506 is the developer 354. For slower and more accurate processes water can be added to the developer (up to 50% by volume) to dilute the developer. The standard development time for the resists mentioned above is 20 to 25 seconds in 100% of developer 354. The developing time can vary depending on the resist parameters. It is important to check the quality of the whole patterning process under microscope after developing the resist.

Gold and Chromium Etching: Once the resist is developed, the exposed part of the photoresist is dissolved in step 120 to expose the metallic Cr/Au layer 60. These bare metallic areas can be stripped by immersing the substrate in gold etchant, and then chromium etchant. The standard chromium etchant is a mixture of nitric acid, ceric ammonium nitrate and water. The etching rate is about 80 nm/min when the solution is fresh. The gold etchant is a solution of 400 gm KI, 200 gm $I_2$ and 1000 mL of water. The etching rate with this solution is 300 nm/min. Since etching process is an isotropic process and it can etch in horizontal direction (under-cutting) as much as vertical direction, it is important to make sure that under-cutting is under control. This control can be implemented by accurate timing. For substrates in this study, the gold etching time was 30 to 35 seconds and chrome etching was 20 seconds. It is important to note that this speed varies with thickness, age of the etchant, temperature and other parameters.

Glass Etching: If the patterning process is to create channels on glass substrates, after gold and chrome etching, glass etching process starts in step 122. Since glass has significant amount of Si—O bonds, the etchant solution is generally hydrofluoric acid (HF) which attacks this bond aggressively. Because of presence of other metals in glass another acid like HCL or HNO3 should be added to the solution to convert this insoluble metal fluorides to soluble salts to reduce surface roughness. An example of the etchant used in this study is: 20% (volumetric) of 40% HF, 14% of 70% HNO3 and 66% of water. This etchant gives etching speed about 0.4 μm/minute for Borofloat glass. Hydrofluoric acid is extremely dangerous and appropriate safety precautions are mandatory.

The etching speed is determined using the following protocol. The first step is to measure the thickness of the Cr+Au+resist layer using a profilometer. This makes the zero point of measurement and every measurement will be compared with this value. The measurements should be taken from different parts of the substrate and averaged out so that we have better approximation of the thickness of this layer. Now, substrates can be immersed in the etchant solution for exactly 5 minutes. The thickness measurement after 5 minutes gives an approximation of the speed of etching. Following this approximation, the etching time can be estimated. The etchant solution gives about 0.3 μm/minute speed for Borofloat glasses. It is a low etching speed but guarantees a good channel profile. The etching speed depends on many parameters like temperature, spinning speed, concentration or age of the etchant, etc., but even for a constant condition, the etching speed can vary from 0.295 microns/minute up to 3.6 microns/minute. Hence, it is recommended to check the etching speed every 10 minutes.

Following glass etching, in step 124 the photoresist layer is removed using Acetone, while the gold and chrome layers are dissolved using proper etchants as described in the previous section. It is important to ensure that there is no area on the substrate left covered with residual photoresist. Sometimes photoresist in some areas is difficult to remove.

Steps 126 through 136 are similar to steps 110 to 120 describe above, except using mask 104 instead of mask 102, and etching in order to create electrodes 20 and 22 from layer 62 under the photoresist 106. In step 138, substrate 12 is silanized, which may be done using Trichlorosilane, available from Sigma-Aldrich (USA), in order to make channel 16 (not seen) hydrophobic, and the top substrate 14 is then bonded on the bottom substrate 12 in step 140, which is described in more detail below.

Referring to FIG. 7, once all etching processes are completed, the substrates 12 and 14 are diced using a dicing saw to recover the individual microchip parts, and the top substrates 14 seal the channels and connections on the bottom substrate 12. These also provide the connecting wells to access the channels. These wells should be drilled through the glass. Drilling the glass is very difficult due to brittle nature of glass. These holes are usually 1 to 3 mm wide. The ultrasonic drill was found to provides a sufficient circle with minimum chipping, however a conventional drilling method may also be used using, for example, diamond drill bits with 2 mm diameter. A support for holding the substrates was manufactured in the workshop. The drill was a small variable speed drill which could provide a constant load on substrates by an adjustable weight mechanism. The drilling speed was about 500 to 1000 rpm. The quality of the holes obtained using the conventional drilling were not good, but sufficient to supply the fluid into the channel.

Glass Bonding: Two clean flat glass substrates can be fused together fairly strongly without any special treatment. The key is to have both of them very clean, since presence of any particle would form an air gap between the substrates, which may cause leakage of fluid from channels. The first step is to make the glass surface clean and hydrophilic using water-soap solution. This would help two surfaces to stick to each other when they come to contact. Then the substrates should be cleaned using a high pressure washing system. The washing procedure followed by high speed drying will prepare the surface for bonding. When two substrates are ready, they can be brought to contact, using eyeball alignment if the features are big, or using the microscope. Using a microscope to align the substrates can be very difficult, so usually it is better not to have any feature on the top substrate. Two clean glass substrates can form a strong bond using this technique; however, this bond is not a permanent bond. To make the bond permanent, the chips may be heat treated in a furnace at up to 500° C. for about two hours. However, the problem with this permanent bonding is that, the high temperature oxidizes the electrodes. The solution to this problem may be to use a furnace with nitrogen gas and ensuring that the nitrogen is injected to the channels.

In the claims, the word "comprising" is used in its inclusive sense and does not exclude other elements being present. The indefinite article "a" before a claim feature does not exclude more than one of the feature being present. Each one of the individual features described here may be used in one or more embodiments and is not, by virtue only of being described here, to be construed as essential to all embodiments as defined by the claims.

Immaterial modifications may be made to the embodiments described here without departing from what is covered by the claims.

We claim:

1. A microfluidic platform for determining characteristics of a thin film, the microfluidic platform comprising:
    a first channel formed in a substrate, the first channel being connected to a first reservoir for supplying a controlled amount of a first fluid to the first channel;
    a second channel formed in the substrate, the second channel being connected to a second reservoir for supplying a controlled amount of a second fluid to the second channel;
    a third channel formed in the substrate, the third channel being connected to a third reservoir for supplying a controlled amount of a film forming liquid to the third channel;
    the first channel, second channel and the third channel being arranged to intersect each other at a common point, such that the first fluid supplied by the first channel and the second fluid supplied by the second channel emulate emulsion droplets at the common point;
    an outlet microchannel for draining fluid from the common point;
    a first electrode in the first channel;
    a second electrode in the second channel; and
    a measuring device connected to the first electrode and the second electrode for measuring an electrical property of a thin film formed of the film forming liquid at the common point.

2. The microfluidic platform of claim 1 in which at least one of the first fluid and the second fluid is an aqueous fluid and the film forming liquid is oil.

3. The microfluidic platform of claim 1 in which each cross-sectional dimension of each of the first channel, the second channel and the third channel at the common point is less than 50 microns.

4. The microfluidic platform of claim 1 in which each cross-sectional dimension of each of the first channel, the second channel and the third channel at the common point is less than 10 microns.

5. The microfluidic platform of claim 1 in which each cross-sectional dimension of each of the first channel, the second channel and the third channel at the common point is less than 5 microns.

6. The microfluidic platform of claim 1 in which at least one of the first channel, the second channel, the third channel, and the outlet channel comprises flow controls for controlling the at least one of the pressure and the flow of fluid through the common point.

7. The microfluidic platform of claim 6 in which the flow controls comprise one or more of pumps, valves, check valves, and channel configurations.

8. The microfluidic platform of claim 1, further comprising a voltage source for applying an electric potential difference across the electrode in the second channel and an electrode in the third channel.

9. The microfluidic platform of claim 8 in which the voltage source is configured to apply a ramped DC electric potential difference for rupturing the thin film.

10. The microfluidic platform of claim 8 in which the voltage source is configured to apply an AC electric potential difference superimposed on a DC electric potential difference.

11. The microfluidic platform of claim 10 in which the voltage source is configured to vary at least one of the frequency and amplitude of the AC electric potential difference over time according to a predetermined algorithm.

12. The microfluidic platform of claim 1 in which each of the first channel and the second channel taper toward the common point.

13. The microfluidic platform of claim 1 in which fluid contacting surfaces of the first channel and the second channel are hydrophilic, and fluid contacting surfaces of the third channel are hydrophobic.

14. A microfluidic platform for determining characteristics of a thin film, the microfluidic platform comprising:
 a first channel formed in a substrate, the first channel being connected to a first reservoir for supplying a controlled amount of a first fluid to the first channel;
 a second channel formed in the substrate, the second channel being connected to a second reservoir for supplying a controlled amount of a second fluid to the second channel;
 a third channel formed in the substrate, the third channel being connected to a third reservoir for supplying a controlled amount of a film forming liquid to the third channel;
 the first channel, second channel and the third channel being arranged to intersect each other at a common point;
 an outlet microchannel for draining fluid from the common point;
 a first electrode in the first channel;
 a second electrode in the second channel; and
 a measuring device connected to the first electrode and the second electrode for measuring an electrical property of a thin film formed of the film forming liquid at the common point.

\* \* \* \* \*